United States Patent [19]

Mednikov et al.

[11] Patent Number: 5,601,743
[45] Date of Patent: Feb. 11, 1997

[54] APPARATUS FOR DETERMINING THE SOLID CONTENTS OF A SLUG BY INDUCTION HEATING

[75] Inventors: Felix Mednikov; Karl Wisspeintner, both of Ortenburg, Germany; Walter Uhlmann, Mörschwil, Switzerland

[73] Assignee: Bühler AG, Uzwil, Switzerland

[21] Appl. No.: 534,061

[22] Filed: Sep. 26, 1995

[30] Foreign Application Priority Data

Apr. 27, 1995 [CH] Switzerland ................... 01208/95

[51] Int. Cl.$^6$ ................................................ H05B 6/06
[52] U.S. Cl. .................... 219/635; 219/663; 219/665; 219/632; 219/674; 266/90; 266/129; 373/145
[58] Field of Search .................... 219/663, 665, 219/666, 667, 668, 677, 635, 637, 653, 632; 266/129, 78, 90, 91, 92, 93, 94; 373/145, 148

[56] References Cited

U.S. PATENT DOCUMENTS

| | | | |
|---|---|---|---|
| 3,136,876 | 6/1964 | Crosthwait | 219/665 |
| 3,742,179 | 6/1973 | Harnden, Jr. | 219/667 |
| 4,317,979 | 3/1982 | Frank et al. | 219/632 |
| 4,668,851 | 5/1987 | Kupper | 219/665 |
| 4,795,886 | 1/1989 | Carter, Jr. | 219/665 |
| 5,438,181 | 8/1995 | Volkmann et al. | 219/635 |
| 5,477,035 | 12/1995 | Matsumoto et al. | 219/635 |

FOREIGN PATENT DOCUMENTS 2506867  9/1976  Germany.

OTHER PUBLICATIONS

German Journal "Giesserei", 80 (1993), No. 4/ Feb. 22, pp. 111 and 112.

*Primary Examiner*—Philip H. Leung
*Attorney, Agent, or Firm*—Martin A. Farber

[57] ABSTRACT

In order to determine the contents of solids in a heated elongated slug of thixotropic metal having a longitudinal axis, there is an apparatus comprising an inductive heating coil with electrical winding. Moreover, a sensor includes at least one measuring coil arranged between the heating coil and the slug. This sensor provides an output signal which corresponds to the contents of solids demanded.

21 Claims, 2 Drawing Sheets

APPARATUS FOR DETERMINING THE SOLID CONTENTS OF A SLUG BY INDUCTION HEATING

FIELD OF THE INVENTION

The present invention is in the field of thixotropic metals having a desired solid contents, and their processing.

BACKGROUND OF THE INVENTION

The solid contents influences highly the processability of such metals and the quality of the final products. It is known that there is a relationship between the melting temperature applied and the eventual solid contents of the slugs. However, the temperature of the hot slugs is not easy to determine. Moreover, the ranges within which a thixotropic behaviour occurs are relatively narrow, thus demanding a high accuracy in measuring temperatures.

In the German Journal "Giesserei", 80 (1993), No. 4/February 22, pp. 111 and 112, an arrangement is described wherein a measuring signal being in direct relationship to the solid contents is obtained by a magnet situated near the lower front surface of the slug and measuring an eddy current.

In fact, this reference is a report about an experimental arrangement at the Technical University of Brunswick (Germany) rather than a field test out of the practice. For to practice, this arrangement is hot suited for several reasons, as tests of the inventors have proved.

First, the lower front surface of a slug, in general, is just that onto which the slug shall stand, because otherwise difficulties will result to hold it. If this surface is contacted with a supporting surface, there is a heat exchange whereby just the surface whose temperature is measured has not that solid contents which is contained in the upper part of the slug. Furthermore, there can be differences in solid contents in radial direction due to the progress in heating up the slug from the exterior to the interior. A further factor may consist in possible interferences of the eddy currents measured by the inductive heating coil, although an arrangement of the sensor at the front surface involves a certain distance from this heating coil.

Therefore, it is a drawback of this, in itself, good idea that the measuring results are not reliable in all cases due to various factors to which bad conditions for handling the slug will add, if its lower front surface shall be used for measuring.

SUMMARY OF THE INVENTION

It is, therefore, an object of the present invention to improve the conditions for handling the slug inspite of using a magnetic sensor, and preferably to enhance the reliability of measurements.

This object is achieved, by an apparatus which comprises not only an inductive heating coil, but also a sensor including at least one measuring coil arranged between the heating coil and the slug which provides an output signal corresponding to the solid contents of the slug.

Thus, by arranging the sensor between the heating coil and the slug the respective bottom surface of the slug is free for setting up. In addition, there is more constructive freedom with respect to the sensor, because the latter can be easier formed in such a manner that it measures not just ranges where temperature is affected by external influences, as it is the case with the lower front surface of the slug, and not only by the heating coil. Because it is just the question of the solid contents which is in a strict relationship with the heating temperature.

The sensor might be arranged in any position between the heating coil and the slug, e.g. along one of the generatrices of the slug which is generally (but not forcibly) cylindric. It is preferred, however, if the measuring coil is arranged and wound around the slug, because in this way measuring is effected round about the slug over the entire periphery, and, thus, a more reliable measuring signal will be obtained. Certainly to the same end, it would be possible to form the sensor with a plurality of coils distributed over the periphery of the slug, for example extending along the generatrices or being helically wound over a predetermined angular range. However, it will be clear that the above preferred arrangement is simpler and less expensive.

Nevertheless, a plurality of coils can be favorable if they are arranged in pairs, and the apparatus has an arithmetic circuit which receives the output signals of the measuring coils thus rendering measurement more accurate and/or providing a facility for a compensation of temperature differences along the slug.

As just mentioned, such a compensation may provide a facility for taking into account temperatures at different locations of the slug, on the one hand, but also the facility of a compensation of influences of the inductive heating coil onto the sensor. For the latter case, it is advisable that the windings of the measuring coils are wound in opposite senses.

In order not to thermically stretch the sensor too much (which was perhaps the reason for the arrangement of the sensor at the front surface in the prior art), a heat shield may be interposed between the slug and the sensor. As heat resistant materials, generally ceramic materials are used, but is surprisingly turned out that these are not up to the thermal stresses so that preferably a non-ceramic material, such as a mica containing material, is used.

In the case of a compensating arrangement for compensating for differently acting heat onto said at least two measuring coils, various embodiments are possible, i.e. alternately an electronic compensation or a special physic construction, the latter being simpler to design, such as in form of a cooling arrangement which ensures, e.g. by cooling via a cooling channel, that it temperatures are equalized. Of course, both approaches could be embodied together.

By the invention, a compact arrangement of sensor and slug is not only facilitated, but is practically forced so that the sensor is radially spaced from said slug only by 5 to 25 mm, and more preferably by 8 to 20 mm. In this way, a measurement free of interferences and more reliable will be obtained.

BRIEF DESCRIPTION OF THE DRAWINGS

Further details of the invention will become apparant from the following description of embodiments schematically shown in the drawings, in which.

As has become known from DE-A-25 06 867, slugs 1 are set up in an equally spaced manner on set up surfaces or platforms 2 of a turntable 3 intermittently driven by a motor M in the direction of arrow P in order to be inductively heated. To this end, the turntable 3 is arranged beneath inductive heat coils 4 each having an equal or different number and thickness of windings.

As is known per se, different dimension or construction of such coils can result in a desired profile of heating temperatures.

Figure 1:
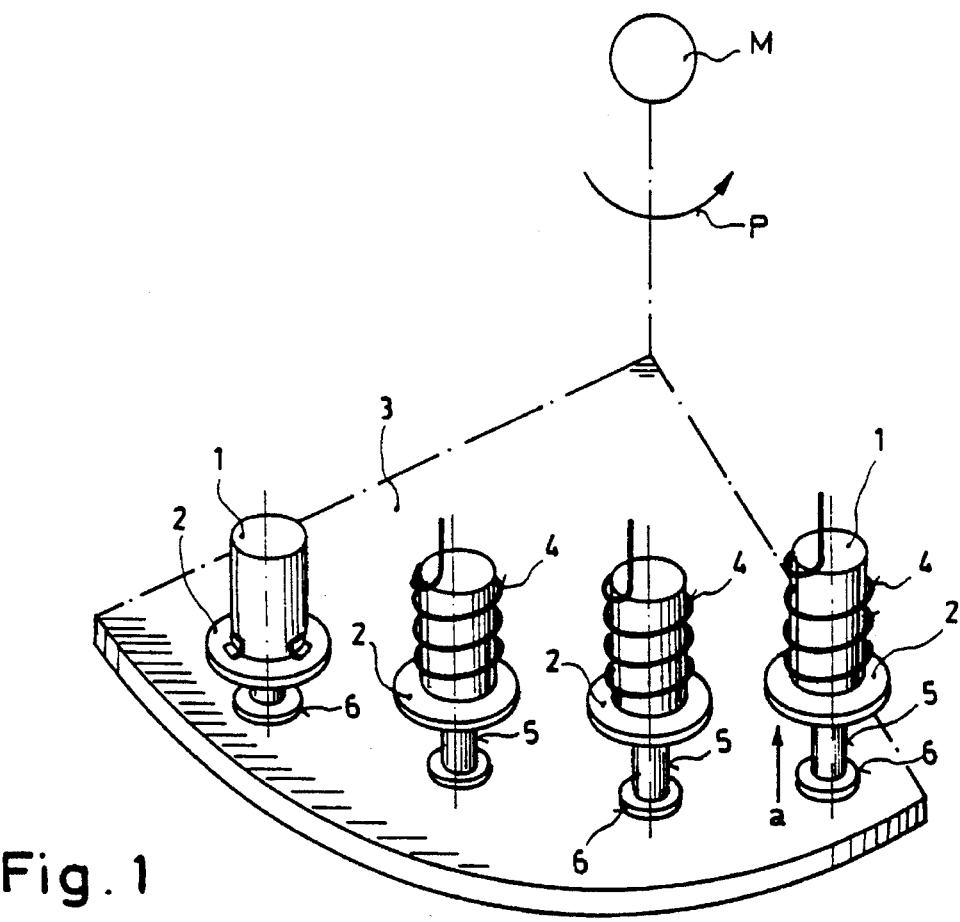
FIG. 1 shows the basic construction of a plant where the invention is applied.

In order to insert the slugs 3 into the interior of the coils 4, either the latter can be lowered, or the platforms 2 can be raised and lowered, which is preferred, by means of a driving arrangement, such as by cams situated below the turntable 3, optionally also by individual fluidic drives including piston and cylinder units. FIG. 1 shows clearly that each platform 2 is secured to a displaceable rod 5 each being guided by a respective bushing 6, and that these rods 5, when seen from the left to the right, are raised in the sense of arrow a to plunge into one of the coils 4 from which they are removed by lowering the platforms 2 after a predetermined preheating, heating and afterheating period, and are conveyed to the next heating coil 4 by rotating the turntable 3 by one step and finally to a casting or forging apparatus.

It will be understood that the invention is not restricted to the use of a plurality of coils 4 and that only a single one could be employed for heating, but the use of several coils 4 is conventional in the respective field to speed up the supply of heated slugs to a shaping machine. Furthermore, it will be evident that the rods 5 could be constructed as shafts provided with a rotary drive, particularly if the slugs are conveyed through individual heating zones (or even through a single one) formed by inductive heating coils located laterally of the path of the slugs, thus avoiding raising and lowering of the platforms 2. Moreover, it will also be clear that, although the upright position of the slugs 1 is preferred, it would also be possible to heat them in a horizontal position. In addition, it might be useful if the platform surfaces 2 have about the size or the diameter of the slugs 1 in order to be able to insert the latters deeply into the heating coils 4, as is shown in FIG. 2.

Figure 2:
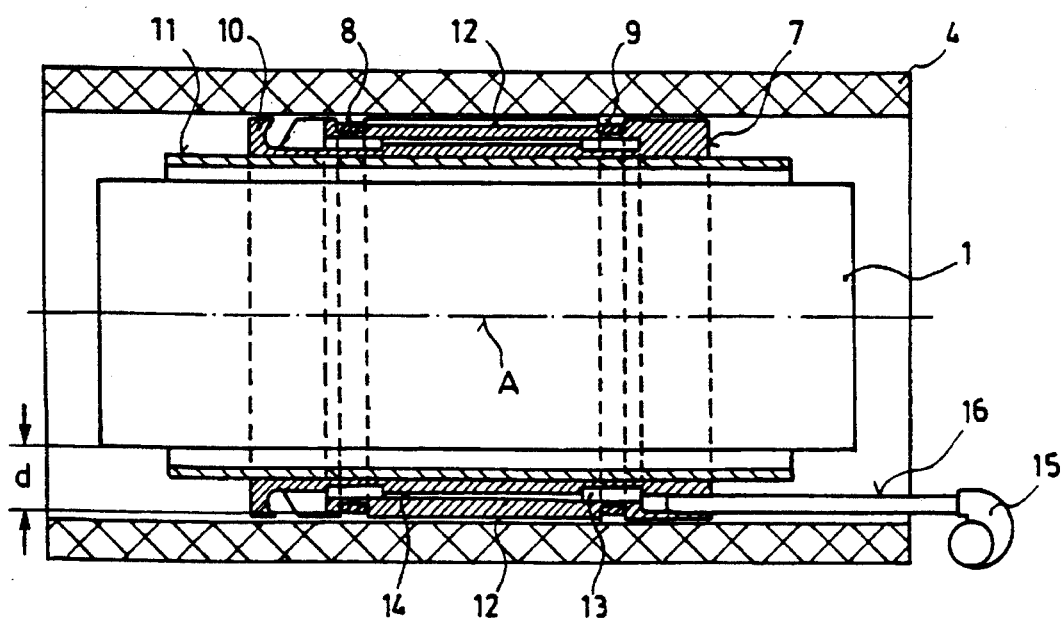
FIG. 2 illustrates a detail of this plant in accordance with the invention.

FIG. 2 illustrates the construction in the region of the inductive heating coils 4 according to a preferred embodiment of the invention where the platform 2 assigned to the slug 1 is not depicted, since also heating in a horizontal position is possible.

In order to be able to control heating of the slugs so that a predetermined solid contents in the slugs 1, which are then thixotropic, is ensured, a sensor 7 is associated to the heating coil 4. In the embodiment shown and preferred, the sensor 7 consists of two measuring coils 8 and 9 which are wound around a spool 10 which electrically isolates both coils 8, 9 from each other.

By these two measuring coils 8, 9 axially spaced from each other (with respect to axis A of the slug 1), first the temperatures (i.e. the temperature dependent changes in inductivity due to different contens of solids and liquid) are sensed in different regions of the slug 1 so that alone from this arrangement a greater reliability of measuring values will result. In addition, it gives the possibility of compensating possible influences of the inductive Heating coil 4 to the measuring coils 8, 9 by having opposite windings in the coils 8, 9, e.g. one to the right and one to the left. This is (in contrast to the prior art) a great advantage in the practice of the present invention, in particular since the coils may be arranged or even are arranged very closely to the slug 1, on the one hand, and to the heating coil 4, on the other hand (which gives also a very compact construction). Thus, this represents a further measure for enhancing a higher exactness and reliability of the measurement results.

When we speak about a very close arrangement, it should be noted that experiments with a radial space d between the sensor 7 or the coils 8, 9 and the slug 1 of only 5 to 25 mm gave excellent measurement results. The most reliable measuring values were obtained with a radial space or distance d of 8 to 20 mm.

Although it would be possible, for example, to provide different distances d for the two coils 8, 9 and to construct them in a different way, it will normally be more advantageous to construct them equally and to keep them in the same radial distance d. It would be conceivable to arrange them in a radial space from each other, for example in the same plane, but this is normally not preferred.

As can be seen, the windings of the coils 8, 9 surround the slug 1 and are coaxially arranged with respect to its axis A which constitutes a preferred embodiment of the invention. It is also conceivable to construct the coils 8, 9, e.g. as flat windings, which may be arranged only at one longitudinal side of the slug 1, in which case it may be desirable, to rotationally drive the platforms 2 (FIG. 1).

It is advantageous to protect the sensor 7 against too much heat by a heat shield 11 situated between the sensor 7 and the slug 1, the heat shield 11, in case the measuring coils completely surround the slug 1, being suitable formed as a hollow cylinder. The choice of material for the heat shield has turned out to be problematic. The reason is mainly that it should not have too thick a wall in order to obtain a reliable measurement. With the smallest possible wall thicknesses, however, conventional ceramic materials, such as refractory materials, tend to cracking and rupture. It has been found that a non-ceramic material, particularly mica containing material, satisfies the best the demands.

Ba the heat shield 11, not only too high temperatures acting onto the sensor 7 are avoided, but, in addition, the temperature within the annular space between the heat shield and the heating coil 4 is equalized which is a further benefit of this arrangement. Furthermore, there will be more freedom in selecting the material for the spool 10, because it is no longer exposed to such a high thermal stress, and, thus, must not really be particularly heat resistant. In this way, the heat shield constitutes another measure for enhancing exactness and reliability of the measurement results. If, in some cases, there would occur, nevertheless, different temperatures affecting the measurement result, a conventional temperature compensating circuit could be inserted into the circuit of the two coils 8, 9.

A simpler temperature compensation, however, is achieved by physical means, such as a cooling arrangement or the two coils 8, 9 or the sensor 7, respectively. To this end, at least one cooling channel 12 is provided within the spool 10 and extends suitably helically around the spool to cool its entire peripheral surface. Alternatively, cooling fluid is distributed from a distributing annular channel 13 into several cooling channels 14 extending along the generatrices (i.e. parallel to the axis A) or over a limited angular range. The cooling fluid is preferably air, because, being electrically non-conductive, it is quite safe. Air is supplied from a suitable source, such as a pump, a storage container or a fan 15 through a supply channel 16 connected to the cooling channel 12 of the spool. Optionally, convection air flowing through with an upright position of the slug (see FIG. 1), which is caused by heating the slug, thus avoiding a forced supply of a cooling medium.

Discharge of heated air is either effected at the opposite end of the spool, or there are discharge channels which, for example, extend parallel to the channels 14, and which transport port the air to the same side of the spool 10 from which supply is effected. Of course, in a closed cooling system, also water or any other cooling liquid or gas could be used. For dissipation of heat, the use of cooling vanes is likewise possible.

Figure 3:
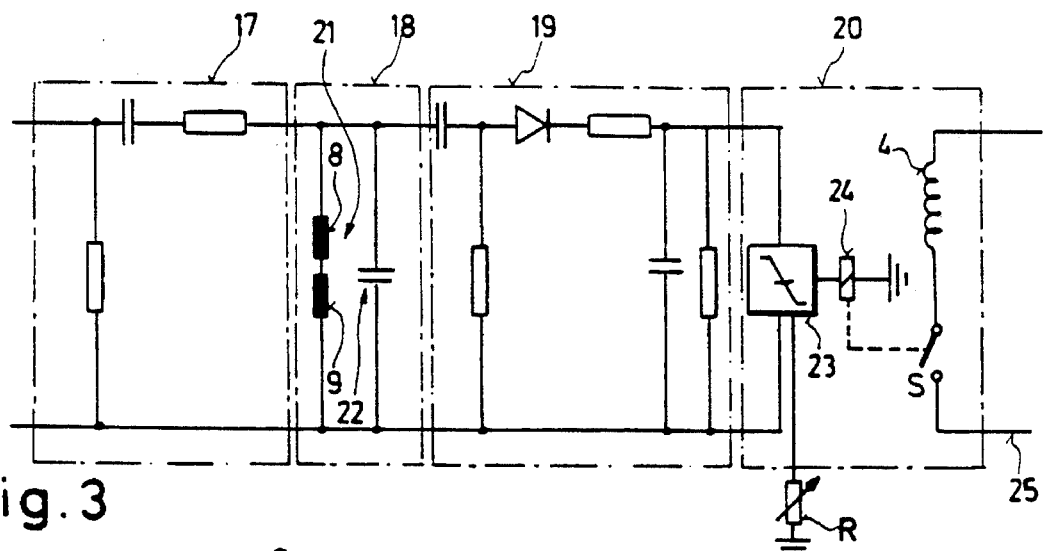
FIG. 3 represents a circuit diagram assigned to the arrangement of FIG. 2 in accordance with an advantageous embodiment.

The circuit shown in FIG. 3 wherein, above all, the measuring coils 8, 9, but according to a preferred embodiment also at least one heating coil 4 is connected, is structured to comprise a supply circuit 17, the very measuring circuit 18, a rectifier portion 19 and a control portion 20. While the supply circuit 17 may be adapted to the requirements in accordance with the special knowledge of those skilled in the art, the measuring circuit 18 is preferably constructed as an oscillating circuit. Therein, the coils 8, 9 are connected in a branch of the measuring circuit in an arithmetic circuit 21, preferably in a summing circuit or summer, i.e. in series. This arithmetic circuit has the purpose to compensate for differences of the measuring values of both coils 8, 9. It can be seen that the circuit shown is extremely simple, it will be understood, however, by those skilled in the art that other mixing circuits and even differential connections (using the difference for correction purposes) are likewise possible. In that the impedances of both coils add to each other in the summer circuit shown, differences of measurements of both coils 8, 9 due to accidental deviations and to other circumstances are compensated.

The coils 8, 9 connected in this manner are preferably within an oscillating circuit comprising a capacitance 22. Therefore, depending on the degree of liquefaction or on the solid contents within the slug 1, a more or less powerful oscillation will result, i.e. either larger or smaller amplitude. If one assumes the oscillation amplitude to be 100% when the slug has just been inserted into the heating coil 4 and is completely in solid state, changes of this amplitude may be either expressed as percentages of it or may be expressed as a percentage of solid content, as will explained later with reference to FIG. 4. Of course, also the absolute values of the impedances of coils 8, 9 at the output of the arithmetic circuit 21 could be directly used as a measuring signal, without the necessity of influencing the oscillator circuit. Moreover, other transformations and forms of the measuring signal would be conceivable, e.g. in a digital form.

In the present embodiment of FIG. 3, a smoothing circuit or rectifier portion 19 is connected to the measuring circuit 18 and transforms merely the measuring signal of circuit 18 so that an integral value is obtained from the oscillations of oscillating circuit 18. This results in an integrated signal s at the output, the course over time of which during heating of the slug 1 being illustrated in FIG. 4.

The signal s, thus transformed, could be used for effecting a manually operated control process by reading it and manually controlling heating by at least one heating coil 4 and terminating it when the desired solid contents is attained. However, it is preferred to do this automatically by supplying the signal s to the control circuit 20.

In a simplified embodiment of FIG. 3, this control circuit 20 comprises only a threshold switch 23 whose output is connected to a magnetic coil 24 for actuating a switch S. The switch S is connected in series with the heating coil 4 in its circuit 25. If the signal s falls below the threshold value of the threshold switch 23, the switch S is opened, and the heating coil 4 is separated from any supply of current. The threshold value of the threshold switch may be suitably adjusted to the solid contents of the slug 1 desired by means of an adjustment resistance R from outside.

Figure 4:
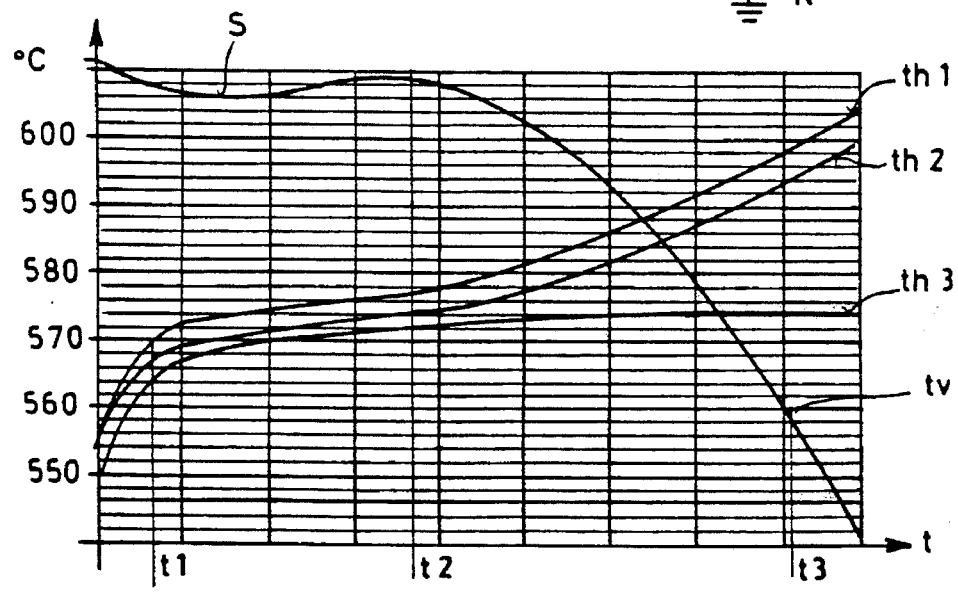
FIG. 4 depicts the signal s of FIG. 3.

From FIG. 4, the result of an experiment for showing the signal s may be seen, the abscissa indicating time, whereas the ordinate gives the temperature of the slug 1 (at left), on the one hand, and the solid contents in percentages within the slug 1 at right, on the other hand, (instead also the liquid contents could be chosen). Three thermoprobes (pyrometer) for measuring the temperature of the slug 1 have been applied to the outside that is in a central region as well as more inside within the region of the axis A. Thus, the curve th1 corresponds to the temperature at the periphery where heating is effected, and which, therefore, is higher than the other temperatures. The curve th2 corresponds to the temperature in about the region of r/2 of the slug 1, and the curve th3 is measured directly in the region of the axis A.

It may be seen that heating was effected quite quickly within an initial period t1. As soon as there is a noticeable liquid contents there is a small bent of the signal s while the heating curves become flattened at the end of time period t1. With the beginning of time period t2, the signal s lowers significantly with further heating, i.e. the solid contents diminishes so that it is only the question what solid contents is desired to determine the moment of interrupting further heating, in particular since the signal s is quite unambigous and reproducible. For example, the resistance R of FIG. 3 can be adjusted so that opening of the switch S is effected when the signal s has reached a threshold value tv.

Figure 5:
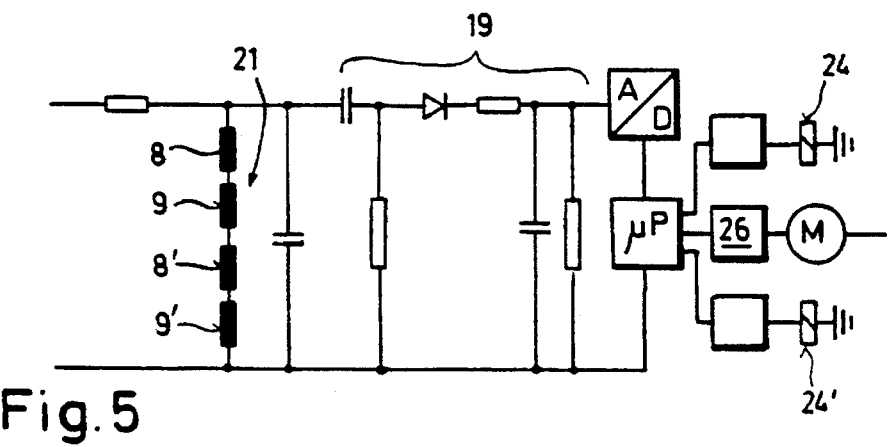
FIG. 5 is further circuit embodiment in a representation similar to that of FIG. 3.

For the reasons explained above (i.e. the compensation facility) an arrangement of the measuring coils 8, 9 in pairs is particularly desirable, although an odd-numbered arrangement, for example with only one coil, would be conceivable. FIG. 5 illustrates another embodiment where two pairs of measuring coils 8, 9, 8' and 9' are connected in a common summer circuit. With respect to FIG. 2, these coils 8, 9, 8' and 9' are distributed over the length of the slug 1, i.e. parallel to the direction of axis A. It should be noted that it is most suitable, if all coils have the same characteristics with respect to number of windings and to impedance.

After smoothing through the circuit 19, the transformed measuring signal s is supplied, in this embodiment to an analog to digital converter A/D whence it is supplied in a digitalized form to a micro-processor µP or to an equivalent circuit. Thus, several output lines for controlling different components could be connected to the microprocessor µP.

In this way, it is possible to control the motor M for driving the turntable 3 (FIG. 1) via a motor control stage 26. Moreover, signal shaping stages 27 (e.g. monoflops) may be connected for controlling magnets 24, 24' in order to switch off different heating coils at different times. Further and preferred possibilities comprise the arrangement of current control means at the output of the micro-processor µP for modifying the temperature profile of the individual heating coils over time.

Numerous modifications are possible within the scope of the invention; for example, it may particularly be seen from FIG. 4 that the change in the signal s is first relatively slow with a gentle bend. Although threshold switches could be provided in order to determine this point, this can be done in a better and quicker way by arranging a differentiating member which would give a clear signal already within the range of t2 (FIG. 4) which signal could then be evaluated by means of a detector circuit corresponding in construction to the circuits 19 and 20.

What is claimed is:

1. An apparatus for determining the contents of solids in a heated elongated slug of thixotropic metal having a longitudinal axis, the apparatus comprising:

heating means including an inductive heating coil for heating the slug; and sensor means including at least one measuring coil providing an output signal, said at least one measuring coil being comprised of electrical windings;

wherein said at least one measuring coil is enclosed by said heating coil, and encloses a space for receiving said slug;

said output signal is representative of contents of solids of the slug; and said apparatus further comprises solid-content evaluation means responsive to said output signal for determining the contents of solids in the slug.

2. Apparatus as claimed in claim 1, wherein said measuring coil is arranged around said slug upon insertion of the slug in the space of said at least one measuring coil.

3. Apparatus as claimed in claim 1, wherein said sensor means include at least two measuring coils, said evaluation means comprising arithmetic circuit means receiving the output signals of said measuring coils.

4. Apparatus as claimed in claim 3, wherein said measuring coils are axially spaced from each other with respect to said longitudinal axis upon insertion of the slug in the space of said at least one measuring coil.

5. Apparatus as claimed in claim 3, wherein the windings of said measuring coils are wound in opposite senses.

6. Apparatus as claimed in claim 3, wherein said measuring coils are radially equally spaced from said slug upon insertion of the slug in the space of said at least one measuring coil.

7. Apparatus as claimed in claim 3, wherein said arithmetic circuit is a summer.

8. Apparatus as claimed in claim 3, further comprising a compensating arrangement for compensating for differently acting heat onto said at least two measuring coils.

9. Apparatus as claimed in claim 8, wherein said compensating arrangement comprises a cooling arrangement for said measuring coils.

10. Apparatus as claimed in claim 9, wherein said cooling arrangement comprises at least one cooling channel for passing a cooling fluid therethrough.

11. Apparatus as claimed in claim 10, wherein said cooling channel is helically wound around said plug upon insertion of the slug in the space of said at least one measuring coil.

12. Apparatus as claimed in claim 9, wherein said cooling arrangement comprises fluid drive means for attaining a forced flow of cooling fluid.

13. Apparatus as claimed in claim 1, further comprising heat shielding means interposed between said plug and said sensor means upon insertion of the slug in the space of said at least one measuring coil.

14. Apparatus as claimed in claim 13, wherein said heat shielding means is formed from a non-ceramic material.

15. Apparatus as claimed in claim 14, wherein said non-ceramic material comprises mica.

16. Apparatus as claimed in claim 1, wherein said sensor means are radially spaced from said slug by 5 to 25 mm upon insertion of the slug in the space of said at least one measuring coil.

17. Apparatus as claimed in claim 16, wherein said sensor means are radially spaced apart from said slug by 8 to 20 mm upon insertion of the slug in the space of said at least one measuring coil.

18. Apparatus as claimed in claim 1, wherein said evaluation means comprises an oscillation circuit which includes said at least one measuring coil, said oscillation circuit experiencing a change in amplitude with changing solid contents of said slug upon insertion of the slug in the space of said at least one measuring coil, further comprising a detector circuit for determining said change in amplitude.

19. Apparatus as claimed in claim 18, wherein said detector circuit comprises differentiating means.

20. Apparatus as claimed in claim 1, further comprising control means for controlling the energy supply to said heating coil, said output signal being received by said control means.

21. Apparatus as claimed in claim 1, further comprising drive means for conveying said slug along a predetermined path to said heating coil, and control means for controlling said drive means, said output signal being received by said control means.

* * * * *